United States Patent
Bhagavatula et al.

(10) Patent No.: US 10,383,521 B2
(45) Date of Patent: Aug. 20, 2019

(54) NON-CYLINDRICAL HYPOTUBES

(71) Applicant: Corning Incorporated, Corning, NY (US)

(72) Inventors: Venkata Adiseshaiah Bhagavatula, Big Flats, NY (US); Woraphat Dockchoorung, Corning, NY (US); Klaus Hartkorn, Painted Post, NY (US); Mark Alan McDermott, Prattsburgh, NY (US); Stephen Quenton Smith, Lawrenceville, PA (US)

(73) Assignee: Corning Incorporated, Corning, NY (US)

( * ) Notice: Subject to any disclaimer, the term of this patent is extended or adjusted under 35 U.S.C. 154(b) by 412 days.

(21) Appl. No.: 14/932,298

(22) Filed: Nov. 4, 2015

(65) Prior Publication Data
US 2016/0120408 A1    May 5, 2016

Related U.S. Application Data

(60) Provisional application No. 62/074,865, filed on Nov. 4, 2014.

(51) Int. Cl.
*A61B 5/00* (2006.01)
*A61B 1/00* (2006.01)

(52) U.S. Cl.
CPC .......... *A61B 5/0066* (2013.01); *A61B 5/0084* (2013.01); *A61B 2560/0406* (2013.01); *A61B 2562/223* (2013.01)

(58) Field of Classification Search
CPC ................ A61B 5/0066; A61B 5/0084; A61B 2562/223; A61B 2560/0406
See application file for complete search history.

(56) References Cited

U.S. PATENT DOCUMENTS

| 4,681,104 A | * | 7/1987 | Edelman | A61B 18/245 606/15 |
| 5,514,108 A | * | 5/1996 | Stevens | A61M 25/0021 604/264 |
| 6,638,267 B1 | | 10/2003 | Esselstein et al. | |
| 7,989,042 B2 | | 8/2011 | Obara et al. | |

(Continued)

FOREIGN PATENT DOCUMENTS

JP    2001079007    3/2001

OTHER PUBLICATIONS

International Search Report and Written Opinion of the International Searching Authority; PCT/US2015/058928; dated Feb. 18, 2016; 14 Pages.

*Primary Examiner* — Mark Bockelman
(74) *Attorney, Agent, or Firm* — Svetlana Z. Short; Smit Kapadia (57) ABSTRACT

A non-cylindrical hypotube is disclosed, such as for use in OCT and endoscopy. The hypotube is defined by a non-cylindrical, rotationally symmetric tube and has an interior, a proximal-end section with an outer diameter D1, a distal-end section with an outer diameter D3, and a middle section between the proximal-end and distal-end sections and having an outer diameter D2, wherein D2<D1, and D2<D3. The distal-end section is sized to accommodate the optical probe and includes an outer surface with an aperture that allows for optical communication therethrough.

16 Claims, 4 Drawing Sheets

(56) References Cited

U.S. PATENT DOCUMENTS

| | | | |
|---|---|---|---|
| 8,343,076 B2 * | 1/2013 | Sela | A61B 5/06 |
| | | | 600/585 |
| 8,816,247 B1 | 8/2014 | Janardhan et al. | |
| 8,834,510 B2 | 9/2014 | Wilson et al. | |
| 2003/0004412 A1 | 1/2003 | Izatt et al. | |
| 2003/0013952 A1 | 1/2003 | Iizuka et al. | |
| 2005/0187422 A1 | 8/2005 | Maschke | |
| 2005/0250983 A1 * | 11/2005 | Tremaglio | A61B 1/0052 |
| | | | 600/101 |
| 2007/0191682 A1 * | 8/2007 | Rolland | A61B 1/00082 |
| | | | 600/173 |
| 2009/0262361 A1 | 10/2009 | Tanoika et al. | |
| 2010/0217372 A1 | 8/2010 | Lentz | |
| 2013/0116618 A1 | 5/2013 | Chouinard | |
| 2013/0223787 A1 | 8/2013 | Bhagavatula et al. | |
| 2013/0266259 A1 | 10/2013 | Bhagavatula et al. | |
| 2014/0180122 A1 | 6/2014 | Stigsll et al. | |
| 2014/0247455 A1 | 9/2014 | Bhagavatula et al. | |
| 2015/0025369 A1 | 1/2015 | Bhagavatula et al. | |

* cited by examiner

*PRIOR ART*

FIG. 1

*PRIOR ART*

NON-CYLINDRICAL HYPOTUBES

CROSS-REFERENCE TO RELATED APPLICATIONS

This application claims the benefit of priority under 35 U.S.C. § 119 of U.S. Provisional Application Ser. No. 62/074,865 filed on Nov. 4, 2014, the content of which is relied upon and incorporated herein by reference in its entirety.

FIELD

The present disclosure relates to hypotubes, and in particular to non-cylindrical hypotubes, such as those used for optical coherence tomography (OCT) and endoscopy.

The entire disclosure of any publication or patent document mentioned herein is incorporated by reference, including US 2013/0223787 and US 2013/0266259.

BACKGROUND

In OCT and endoscopy, an optical probe attached to an optical fiber is used to relay images from remote interior locations of the body to a user. The optical probe is housed in a hypotube, which in turn is contained within a guide tube, called an "inner lumen." A torque coil is operably attached to an end of the hypotube and causes rotation of the hypotube and the optical probe therein within the inner lumen. The hypotube acts as a bearing for the rotation as well as a protective body for the relatively fragile miniature optics of the optical probe. The inner lumen is flexible so that it can be fed into an orifice of the body and be wended to a desired location within the body.

The flexure of the inner lumen is limited by the size of the conventional cylindrical hypotube. This in turn limits the functionality of the OCT or endoscopy system since a limited bending radius puts restrictions on where the inner lumen can be guided during its use when carrying out a procedure.

SUMMARY

An aspect of the disclosure is a hypotube for operably containing an optical probe. The hypotube includes: a non-cylindrical, rotationally symmetric tube having an interior, a proximal-end section with an outer diameter D1, a distal-end section with an outer diameter D3, and a middle section between the proximal-end section and the distal-end section and having an outer diameter D2; wherein the distal-end section is sized to accommodate the optical probe and includes an outer surface with an aperture; and wherein D2<D3.

Another aspect of the disclosure is the hypotube as described above, and further including: the optical probe operably arranged in the distal-end section relative to the aperture to allow for optical communication therethrough; and an optical fiber operably connected to the optical probe at a fiber-probe interface, with the fiber-probe interface residing within the distal-end section of the hypotube.

Another aspect of the disclosure is a hypotube for operably containing an optical probe operably attached to an optical fiber. The hypotube includes: a non-cylindrical, rotationally symmetric tube having a proximal-end section with an outer diameter D1, a middle section with an outer diameter D2 and a distal-end section with an outer diameter D3; a proximal-end transition region that defines a transition between the proximal-end section and the middle section; a distal-end transition region that defines a transition between the distal-end section and the middle section; and wherein D2<D3.

Another aspect of the disclosure is a hypotube assembly, comprising: an optical probe operably connected to an optical fiber at a fiber-probe interface; a hypotube defined by a non-cylindrical, rotationally symmetric tube having an interior and a proximal-end section with an outer diameter D1, a middle section with an outer diameter D2 and a distal-end section with an outer diameter D3, an outer surface, and an aperture formed in the outer surface, wherein D2<D3; wherein the optical probe is operably arranged in the interior of the hypotube in the distal-end section and is operably disposed relative to the aperture to allow for optical communication therethrough; and wherein the optical fiber passes through the proximal-end section and the middle section such that the fiber-probe interface resides within the distal-end section of the hypotube.

Additional features and advantages are set forth in the Detailed Description that follows, and in part will be readily apparent to those skilled in the art from the description or recognized by practicing the embodiments as described in the written description and claims hereof, as well as the appended drawings. It is to be understood that both the foregoing general description and the following Detailed Description are merely exemplary, and are intended to provide an overview or framework to understand the nature and character of the claims.

BRIEF DESCRIPTION OF THE DRAWINGS

The accompanying drawings are included to provide a further understanding, and are incorporated in and constitute a part of this specification. The drawings illustrate one or more embodiment(s), and together with the Detailed Description serve to explain principles and operation of the various embodiments. As such, the disclosure will become more fully understood from the following Detailed Description, taken in conjunction with the accompanying Figures, in which.

DETAILED DESCRIPTION

Reference is now made in detail to various embodiments of the disclosure, examples of which are illustrated in the accompanying drawings. Whenever possible, the same or like reference numbers and symbols are used throughout the drawings to refer to the same or like parts. The drawings are not necessarily to scale, and one skilled in the art will recognize where the drawings have been simplified to illustrate the key aspects of the disclosure.

The claims as set forth below are incorporated into and constitute a part of this Detailed Description.

Cartesian coordinates are shown in some of the Figures for the sake of reference and are not intended to be limiting as to direction or orientation.

The term "non-cylindrical" is used to describe the hypotube as disclosed herein. The term "cylindrical" as used herein means a three-dimensional object that is obtained by taking a two-dimensional area and projecting it in one direction so that the resulting three-dimensional object has the same cross-sectional size and shape at any location along its length.

The diameters D1, D2 and D3 introduced and discussed below in connection with the hypotube described herein are outer diameters of the hypotube.

Figure 1:
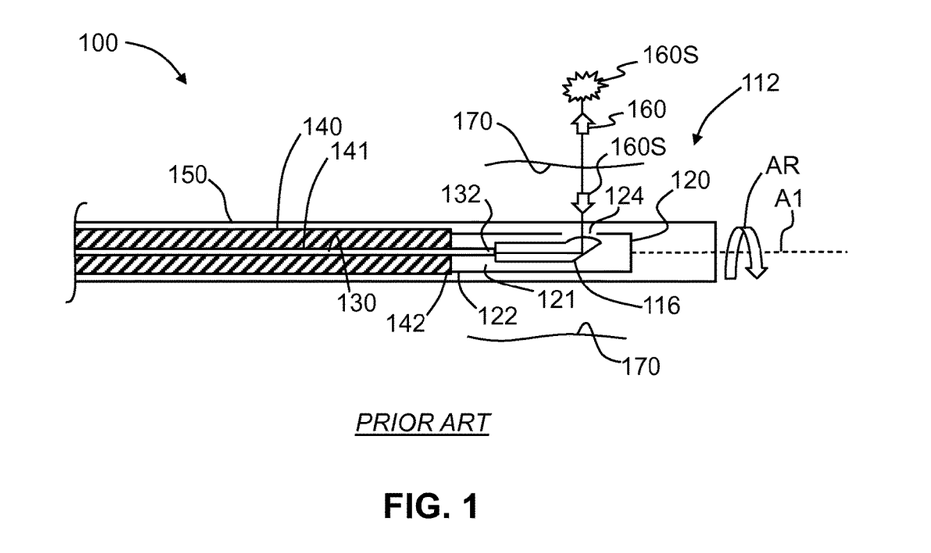
FIG. 1 is a schematic cross-sectional view of an end portion of an example prior-art OCT system.

FIG. 1 is a cross-sectional, close-up view of a portion of a prior-art OCT system 100 showing an end portion 112. The OCT system 100 includes an optical probe 116 that is operably connected to an end 132 of an optical fiber 130. The optical fiber 130 is supported within a channel 141 of a metal (e.g., stainless steel) torque tube 140. A typical torque tube 140 is a multi-coil spring assembly made of a metal such as stainless steel.

Figure 2:
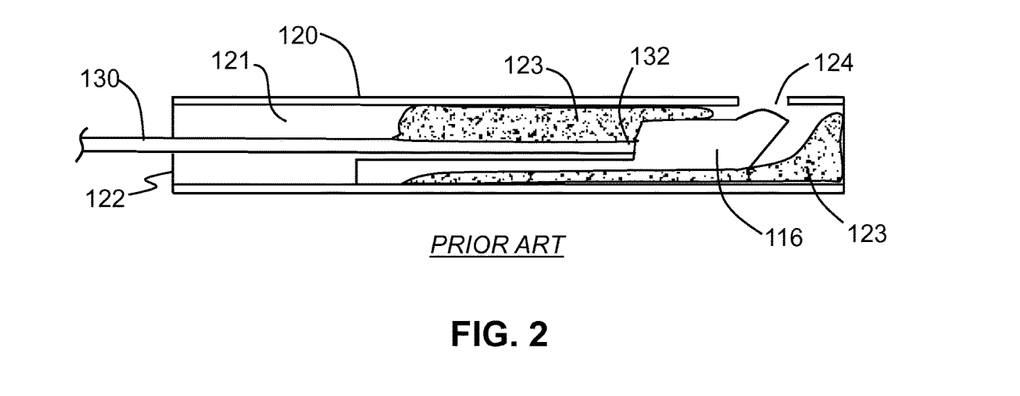
FIG. 2 is similar to FIG. 1 and shows a close-up view of an optical probe contained within a conventional hypotube.

The optical probe 116 resides within an interior 121 of a hypotube 120. FIG. 2 is a cross-sectional view of a prior-art hypotube 120 wherein the hypotube interior 121 contains an example unitary optical probe 116 fixed therein with a bonding material 123. An end portion 122 of hypotube 120 is attached to an end portion 142 of torque tube 140. The hypotube 120 includes an aperture 124 for optical communication of the optical probe 116 through the hypotube. The torque tube 140 and hypotube 120 reside within a guide tube or inner lumen 150 and rotate and axially translate therein, though there is typically some contact between the torque tube and the inner lumen, i.e., there is a close-fit between the torque tube and the hypotube within the inner lumen. The optical probe 116 is fixed to hypotube 120 (e.g., via bonding material 123) and thus rotates with the hypotube.

The inner lumen 150 is transparent to an OCT imaging wavelength of light 160 at least at end portion 112. In an example, a (transparent) balloon (not shown) is used to create space for optical-probe-end portion 112 within a tissue or vessel 170. The optical-probe-end portion 112 of OCT system 100 is inserted into a catheter or endoscope (not shown) for insertion into the body to be examined.

The light 160 originates from a light source (not shown) and travels down optical fiber 130 to end 132. This light 160 exits end 132 of optical fiber 130 and is directed by optical probe 116 through aperture 124 in hypotube 120, through inner lumen 150 and to the surrounding tissue or vessel 170. The light 160 generates scattered light 160S from tissue or vessel 170, and some of this scattered light returns to and is captured by optical probe 116 along the reverse optical path and is directed back to optical fiber end 132. The returned scattered light 160S travels back down optical fiber 130 toward the light source and is then interferometrically processed to generate the OCT image at the OCT imaging wavelength according to methods known in the art.

Figure 3:
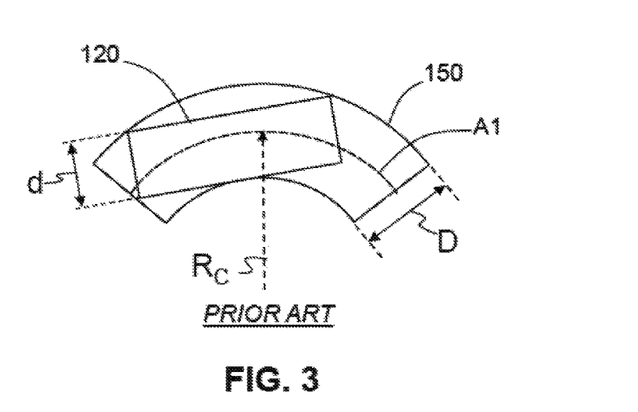
FIG. 3 is a schematic diagram showing a conventional hypotube within a bent inner lumen and illustrating how the minimum or critical bend radius $R_C$ of the inner lumen is determined based on the length and diameter of the cylindrical hypotube and the inside diameter of the inner lumen.

FIG. 3 a close-up view of a bent section of inner lumen 150 showing the conventional hypotube 120 disposed therein. The conventional hypotube 120 is a short cylindrical section of rigid tubing, on the order of 1 cm long. The clearance between hypotube 120 and inner lumen 150 is on the order of 100 microns or so, with a typical value being about 130 microns. Thus, there is a critical (minimum) bend radius $R_C$ for inner lumen 150 below which hypotube 120 cannot be fed therethrough without contacting the walls of the inner lumen and getting stuck. The critical bend radius $R_C$ is measured relative to a central axis A1 of the inner lumen and is given by:

$$R_C = (L/2)^2/[2 \cdot (D-d)] - d/2$$

where L is the length of hypotube 120, d is the diameter of the hypotube, and D is the (inside) diameter of inner lumen 150.

There is a benefit to making the critical radius $R_C$ smaller because a smaller bending radius allows inner lumen 150 to be inserted more easily into tight spaces, thereby increasing the functionality of OCT system 100. There are two main options for making the critical bend radius $R_C$ smaller: either decrease the length L of hypotube 120 or increase the diameter D of inner lumen 150. However, both of these options serve to diminish the bearing and protective functions of hypotube 120. Likewise, making the diameter d of the cylindrical hypotube 120 smaller is not a viable option because it is already considered to be at the minimum size able to accommodate optical probe 116 and optical fiber 130 attached to the optical probe.

Figure 4A:
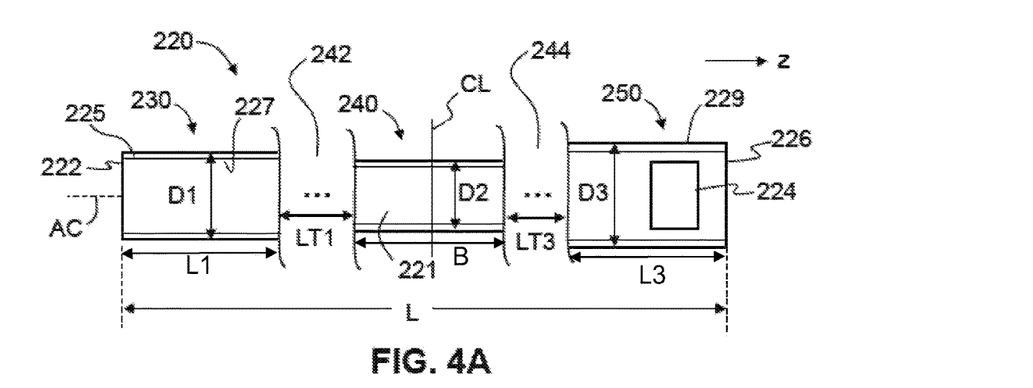
FIG. 4A is a schematic diagram of an example generalized hypotube according to the disclosure, illustrating how the hypotube can be divided up into two or more sections that have different outside diameters.

FIG. 4A is a schematic diagram of an example generalized hypotube 220 according to the disclosure. The hypotube 220 has a central axis AC, an interior 221, a proximal end 222, a distal end 226, and an overall length L, which in an example is in the range from 0.5 cm to 1 cm. The hypotube 220 is defined by a tubular body or "tube" 225 that has an inner surface 227 and an outer surface 229. In an example, hypotube 220 is non-cylindrical and is rotationally symmetric.

In the generalized example of FIG. 4A, hypotube 220 includes three main sections: a proximal-end section 230 with an outer diameter ("diameter") D1, and a length L1, a middle section 240 with an outer diameter ("diameter") D2 and a length B, and a distal-end section 250 with an outer diameter ("diameter") D3 and a length L3. The distal-end section 250 includes an aperture 224 in wall 225 that allows for optical communication therethrough, e.g., when optical probe 116 is operably disposed within interior 221 of hypotube 220. In an example, the length B of the middle section 240 is greater than the length L1 of the proximal-end section 230 and/or the length L3 of the distal-end section 250 (see, e.g., FIGS. 5, 6, 7, 8 and 9, introduced and discussed below).

Figure 5:
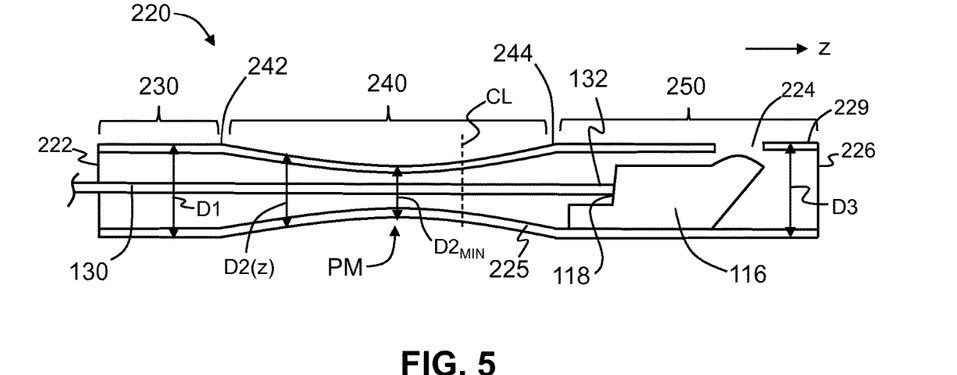
FIG. 5 is a cross-sectional view of an example hypotube wherein the middle section has an hourglass shape defined by a continuously varying diameter.

In an example, D2<D3, while in another example, D2<D1, and D2<D3. In an example, diameter D2 is not constant but varies within at least a portion of middle section 240 as a function of the length of hypotube 220 (i.e., in the z-direction), and can thus be represented in some examples as D2(z) (FIG. 5). In such a case, the diameter D2 can have a minimum diameter, which can be denoted as $D2_{MIN}$ (FIG. 5). The middle section 240 includes a centerline CL that represents the midway location between proximal and distal ends 222 and 226. In one example, the minimum diameter $D2_{MIN}$ occurs at centerline CL, while in another example, the minimum diameter $D2_{MIN}$ is axially displaced relative to the centerline.

In an example, there is a first or proximal-end transition region 242 of length LT1 between proximal-end section 230 and middle section 240. Also in an example, there is a second or distal-end transition region 244 of length LT3 between distal-end section 250 and middle section 240. In another example, hypotube 220 includes both transition regions 242 and 244. In an example, the length LT1 of first transition region 242 can be in the range from 0 mm≤LT1≤2 mm or 0 mm LT1≤1 mm or 0 mm≤LT1≤0.5 mm or 0 mm<LT1≤0.2 mm or 0 mm<LT1≤0.5 mm or 0 mm LT1≤0.2 mm. Likewise, in an example, the length LT3 of second transition region 244 can be in the range from 0 mm≤LT3≤2 mm or 0 mm≤LT3≤1 mm or 0≤LT3≤0.5 mm or 0 mm<LT3≤0.2 mm or 0 mm<LT3≤0.5 mm or 0 mm≤LT3≤0.2 mm.

Note that a transition length of LT1=0 or LT3=0 corresponds to an abrupt transition when the diameters of the adjacent sections are different. In an example abrupt transition regions are not desirable, the lower limit on the range for LT1 and LT3 can be non-zero to avoid sharp edges. In an example, the first and second transition regions 242 and 244 can be curved or flat (e.g., beveled or chamfered). In an example, LT1=LT3, but in general these two transition lengths need not be the same.

In an example, the diameters D1 and D3 need not be constant within their respective proximal-end and distal-end sections 230 and 250. In an example, diameters D1 and D3 represent maximum diameters. In another example, diameters D1 and D3 are constant. In an example, diameters D1, D2 and D3 are each constant, and the only variation in diameter in hypotube 220 occurs in one or both of first and second transition regions 242 and 244.

In an example, D1=D3 while D2<D1, and thus D2<D3. In an example, the diameter D2 is in the range 0.5 mm≤D2≤1.2 mm or in the range 0.5 mm≤D2≤1.0 mm. In an example, proximal-end section 230 is made larger than middle section 240 (i.e., D1>D2) to more easily accommodate connecting to torque tube 140 (see FIG. 9). In an example where D3>D2, distal-end section 250 is made larger than middle section 240 to accommodate optical probe 116. In an example, the diameters D1 and D3 are no larger than the diameter d of a conventional cylindrical hypotube 120, while diameter D2 is smaller than the conventional diameter d. Also in an example, the diameter D2 can be made such that at least one of the diameters D1 and D3 can be made larger than the conventional diameter d. An example of a conventional diameter d is 1.27 mm.

In an example, hypotube 220 is made of metal, such as stainless steel. In another example, hypotube 220 is made of a rigid non-metallic material, such as a plastic or polymer. In yet another example, hypotube 220 is made of a material that is not entirely rigid, i.e., has some degree of flexibility.

Figure 4B:
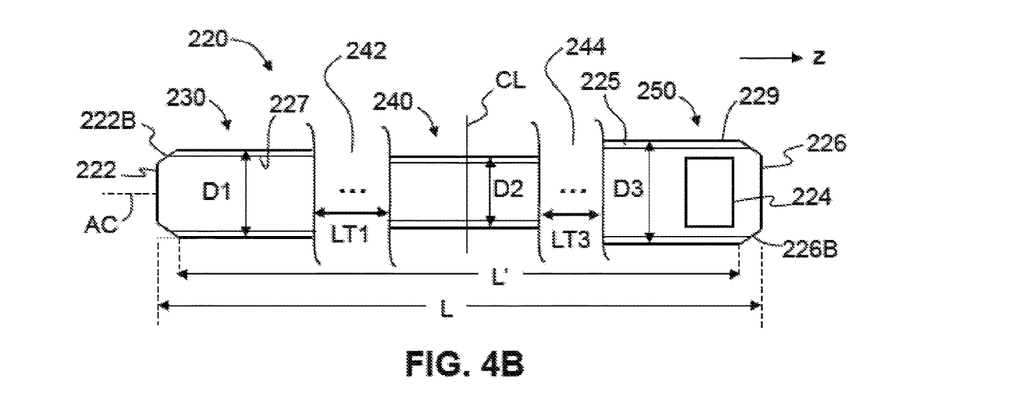
FIG. 4B is similar to FIG. 4A and shows an example hypotube that includes a proximal-end bevel and a distal-end bevel.

FIG. 4B is similar to FIG. 4A and illustrates an example hypotube 220 that includes at proximal end 222 a proximal-end bevel 222B and also includes at distal end 226 a distal-end bevel 226B. The proximal-end and distal-end bevels 222B and 226B help reduce the critical bend radius $R_C$, as discussed in greater detail below in connection with FIG. 8. In one an example, hypotube 220 includes only one of proximal-end and distal-end bevels 222B and 226B, while in another example the hypotube includes both bevels, as shown. The size of proximal-end and distal-end bevels 222B and 226B can be designed to define a select critical bend radius $R_C$. In an example, proximal-end and distal-end bevels 222B and 226B can have any physically realizable dimensions consistent with the proper operation of hypotube 220 as part of an OCT or endoscopic system.

The example configurations of hypotube 220 as disclosed herein take advantage of the fact that the components contained within hypotube interior 221 do not all have the same size. In an example arrangement, the relatively narrow optical fiber 130 passes through proximal-end section 230 and through middle-end section 240 to optically connect to the relatively wide optical probe 116 that resides in distal-end section 250.

FIG. 5 is cross-sectional diagram of an example hypotube 220 according to the disclosure. The example unitary optical probe 116 is shown contained within hypotube interior 221. The optical probe 116 has a rear end 118 that operably engages end 132 of optical fiber 130 to define a fiber-probe interface 135. In the example, middle section 240 has an hourglass shape, wherein the middle diameter D2 varies continuously to a minimum value $D2_{MIN}$ at an axial position PM, which in the example shown is offset from centerline CL. In the example hypotube 220 of FIG. 5, proximal-end and distal-end transition regions 242 and 244 can have relatively short transition lengths LT1 and LT3, and in the example shown, it can be said that LT1=0 and LT3=0.

Figure 6:
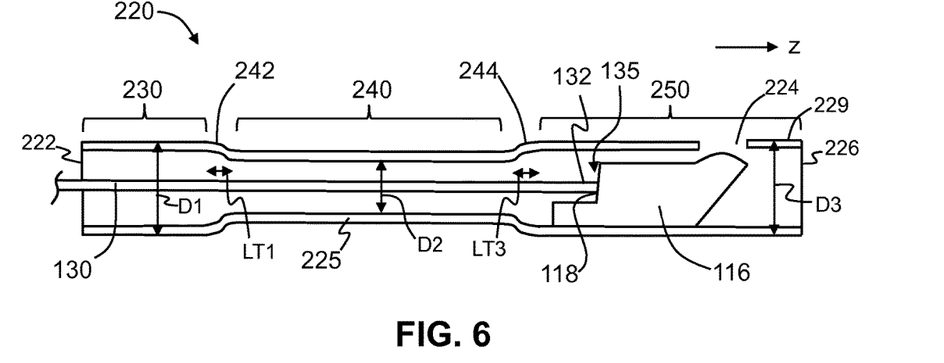
FIG. 6 is similar to FIG. 5 and illustrates an example hypotube wherein a portion of the middle section has a constant radius and the proximal-end and distal-end transition regions are curved to match the larger diameters of the proximal-end and distal-end sections.

FIG. 6 is similar to FIG. 5 and illustrates an example embodiment of hypotube 220 wherein middle section 240 has a constant diameter D2<D1, D2<D3 and has curved or tapered transition regions 242 and 244 that respectively connect to proximal-end section 230 and to distal-end section 250. As noted above, the curved or tapered transition regions 242 and 244 avoid the use of sharp edges or sharp transitions between the different sections.

Figure 7:
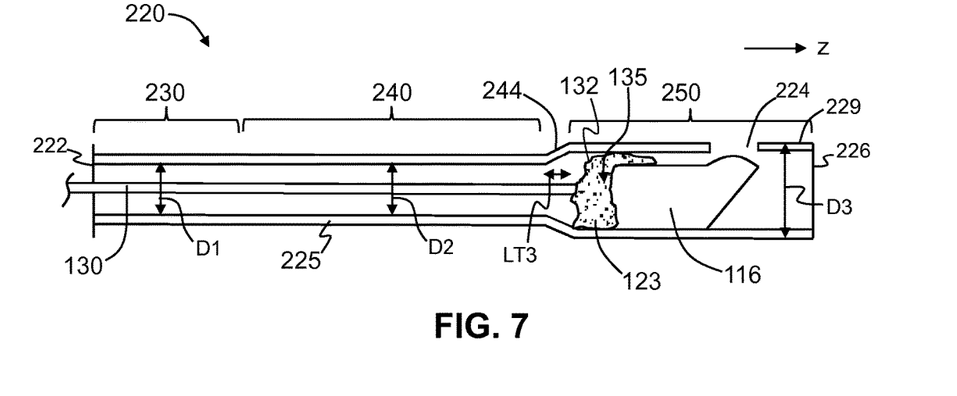
FIG. 7 is similar to FIG. 6 and illustrates an example hypotube wherein the distal-end transition region is linear, and wherein the proximal-end and middle sections have the same diameter.

FIG. 7 is similar to FIG. 6, but wherein D1=D2 so that there is no transition feature in proximal-end transition region 242 that separates middle section 240 and proximal-end section 230. Here, the transition length LT1=0, but there is no discontinuity since D1=D2. Also in the example, distal-end section 250 is made shorter due to having a shorter optical probe 116. In addition, distal-end transition region 244 is shown by way of example as being in the form of a straight bevel.

In an example embodiment, distal-end section 250 of hypotube 220 includes optical probe 116 and fiber-probe interface 135. This configuration is useful in cases where hypotube 220 is made of a flexible material such as plastic. To maintain the imaging quality of the OCT or endoscope system, fiber-probe interface 135 needs to remain in a fixed position. In the example illustrated in FIG. 7, bonding material 123 is provided at optical fiber end 132 and optical probe rear end 118 (see FIG. 6) to ensure that fiber-probe interface 135 remains fixed in place. However, if fiber-probe interface 135 resides at distal-end transition region 244 or within the narrower middle section 240, then there is an increased risk that fiber-probe interface 135 will be disturbed should hypotube 220 bend or flex.

Figure 8:
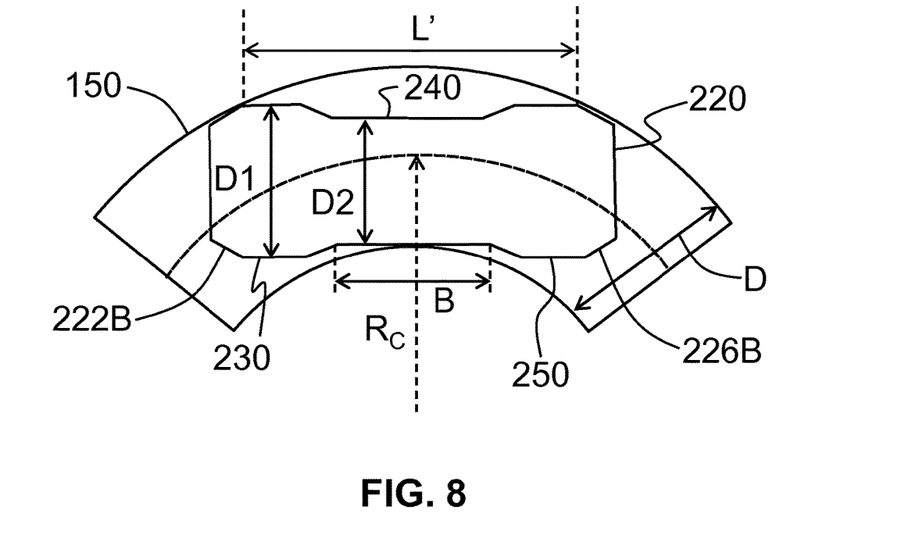
FIG. 8 is similar to FIG. 3 and illustrates an example hypotube based on the example hypotube shown in FIG. 4B, with the hypotube residing within an example inner lumen, and also showing the dimensional parameters involved in the calculation of the critical bend radius $R_C$.

FIG. 8 is similar to FIG. 3 and shows an example hypotube 220, representative of the hypotube shown in FIG. 4B, residing within inner lumen 150. The proximal-end diameter D1 is the same as the distal-end diameter D3. The example hypotube 220 has proximal-end and distal-end bevels 222B and 226B. A length B of center section 240 is shown. The critical radius is given by $R_C=[(L'/2)^2/2D-D1-D2)]-[(D1+D2)/4]$, where L' is the effective length of hypotube 220 as measured between the inside edges of proximal-end and distal-end bevels 222B and 226B.

A prior-art hypotube 120 of length L=10 mm, a constant diameter d=1.27 mm and inner lumen 150 with an inner diameter D=1.4 has a critical bend radius $R_C \approx 95.52$ mm as calculated using the above-described equation for the critical bend radius as described in connection with FIG. 3. For the same inner lumen 150, a hypotube 220 with L'=10 mm, D1=1.27 mm and D2=1 mm has a critical bend radius $R_C \approx 46.6$ mm, as calculated using the equation for the critical bend radius as described in connection with FIG. 8. The critical bend radius $R_C$ for hypotube 220 is about 51% smaller than the prior-art critical bend radius and represents about a 2× bending improvement. To achieve this performance for the example configuration, the value of L'−B is in the range from 3.5 mm to 4 mm.

Generally speaking, the example hypotubes 220 disclosed herein can be configured to have a critical bend radius $R_C$ that is smaller than the corresponding conventional cylindrical hypotube 120 such as shown in FIG. 3. A smaller critical bend radius $R_C$ translates into greater performance and functionality of the particular system (e.g., OCT system or endoscopy system) in which hypotube 220 is used.

Figure 9:
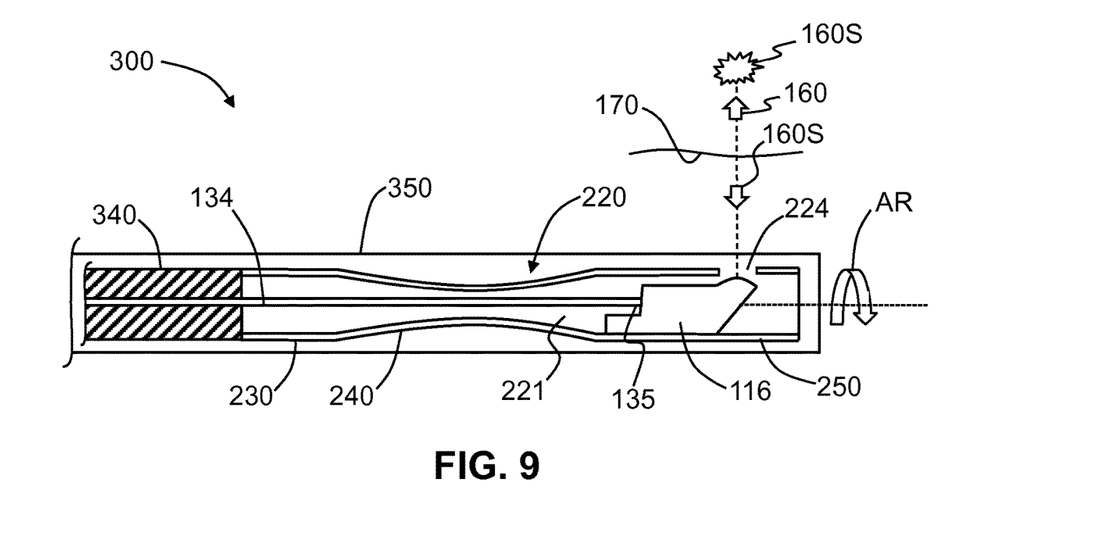
FIG. 9 is similar to FIG. 1 and illustrates an end portion of an example OCT system that employs the hypotube shown in FIG. 5 by way of example.

FIG. 9 is a cross-sectional diagram of an end portion of an OCT system 300 that shows an end portion of a guide tube or inner lumen 350. The inner lumen 350 contains the example hypotube 220 shown in FIG. 5, along with optical probe 116, optical fiber 130 and fiber-probe interface 135. A torque coil 340 is operably connected to proximal end 222 of hypotube 220. The combination of hypotube 220, optical probe 116 and optical fiber 130 constitutes a hypotube assembly.

As discussed above in connection with FIG. 1, light 160 originates from a light source (not shown) and travels down optical fiber 130 to end 132. This light 160 exits end 132 of optical fiber 130 at fiber-probe interface 135 and is directed by optical probe 116 through aperture 124 in hypotube 220, through inner lumen 350 and to the surrounding tissue or vessel 170. The light 160 generates scattered light 160S from tissue or vessel 170, and some of this scattered light returns to and is captured by optical probe 116 along the reverse optical path and is directed back to optical fiber end 132 at fiber-probe interface 135. The returned scattered light 160S travels back down optical fiber 130 toward the light source and is then interferometrically processed to generate the OCT image at the OCT imaging wavelength according to methods known in the art.

It will be apparent to those skilled in the art that various modifications to the preferred embodiments of the disclosure as described herein can be made without departing from the spirit or scope of the disclosure as defined in the appended claims. Thus, the disclosure covers the modifications and variations provided they come within the scope of the appended claims and the equivalents thereto.

What is claimed is:

1. An optical coherence tomography (OCT) system, comprising:

a hypotube comprising a non-cylindrical, rotationally symmetric rigid tube having an interior, a proximal-end section with a length L1 and an outer diameter D1, a distal-end section with a length L3 and an outer diameter D3 and an outer surface with an aperture, and a middle section between the proximal-end section and the distal-end section and having a length B and an outer diameter D2, and wherein the length B is greater than the length L1 and/or the length L3, and wherein D2<D3;

an optical probe operably arranged in the distal-end section relative to the aperture to allow for optical communication therethrough;

an optical fiber operably connected to the optical probe at a fiber-probe interface, with the fiber-probe interface residing within the distal-end section of the hypotube;

a torque coil operably connected to a proximal end of the proximal-end section of the of the hypotube; and an inner lumen that contains the hypotube and the torque coil, wherein the inner lumen has a critical bend radius that is smaller as compared to using a cylindrical hypotube having an outer diameter equal to D3.

2. The OCT system according to claim 1, wherein D2<D1.

3. The OCT system according to claim 1, wherein D1=D3.

4. The OCT system according to claim 1, wherein the outer diameter D2 of the middle section varies as a function of length along the hypotube.

5. The OCT system according to claim 4, wherein the middle section has an hourglass shape.

6. The OCT system according to claim 1, wherein at least a portion of the middle section has a constant outer diameter D2.

7. The OCT system according to claim 1, wherein the middle section transitions to the distal-end section over a distal-end transition region wherein the hypotube varies in diameter over a transition length LT3 in the range 0 mm≤LT3≤0.5 mm.

8. The OCT system according to claim 7, wherein the middle section transitions to the proximal-end section over a proximal-end transition region wherein the hypotube varies in diameter over a transition length LT1 in the range 0 mm≤LT1≤0.5 mm.

9. The OCT system according to claim 8, wherein the proximal-end transition region is either curved or straight, and wherein the distal-end transition region is either curved or straight.

10. The OCT system according to claim 1, wherein the hypotube includes at least one of a proximal-end bevel at a proximal end of the proximal-end section and a distal-end bevel at a distal end of the distal-end section.

11. A hypotube assembly, comprising:

an optical probe operably connected to an optical fiber at a fiber-probe interface;

a hypotube defined by a non-cylindrical, rotationally symmetric tube with an interior and a proximal-end section with an outer diameter D1 and a length L1, a middle section with an outer diameter D2 and a length B, and a distal-end section with an outer diameter D3 and a length L3, an outer surface, and an aperture formed in the outer surface, wherein D2<D3, and wherein the length B is greater than the length L1 and/or the length L3;

wherein the optical probe is operably arranged in the interior of the hypotube in the distal-end section and is operably disposed relative to the aperture to allow for optical communication therethrough;

wherein the optical fiber passes through the proximal-end section and the middle section such that the fiber-probe interface resides within the distal-end section of the hypotube; and an inner lumen that contains the hypotube, wherein the inner lumen has a critical bend radius that is smaller as compared to using a cylindrical hypotube having an outer diameter equal to D3.

12. The hypotube assembly according to claim 11, wherein the hypotube includes at least one of a proximal-end bevel at a proximal end of the proximal-end section and a distal-end bevel at a distal end of the distal-end section.

13. The hypotube assembly according to claim 11, wherein the outer diameter D2 varies along at least a portion of the length of the hypotube within the middle section.

14. The hypotube assembly according to claim 11, further comprising:

a proximal-end transition region that defines a transition between the proximal-end section and the middle section and a distal-end transition region that defines a transition between the distal-end section and the middle section; and wherein the proximal-end transition region has a length LT1 in the range $0 \leq LT1 \leq 1$ mm and the distal-end transition region has a length LT3 in the range $0 \leq LT3 \leq 1$ mm.

15. The hypotube assembly according to claim 14, wherein the length $LT1 \leq 0.5$ mm and the length $LT3 \leq 0.5$ mm.

16. The hypotube assembly according to claim 11, wherein D2<D1.

* * * * *

UNITED STATES PATENT AND TRADEMARK OFFICE
CERTIFICATE OF CORRECTION

PATENT NO.         : 10,383,521 B2
APPLICATION NO.    : 14/932298
DATED              : August 20, 2019
INVENTOR(S)        : Venkata Adiseshaiah Bhagavatula et al.

Page 1 of 1

It is certified that error appears in the above-identified patent and that said Letters Patent is hereby corrected as shown below:

In the Claims

In Column 8, Line 19, Claim 1, before "hypotube" delete "of the".

In Column 10, Line 16, Claim 16, delete "D2<D1." and insert -- D2<D1. -- therefor.

Signed and Sealed this
Twenty-fifth Day of February, 2020

Andrei Iancu
*Director of the United States Patent and Trademark Office*